United States Patent
Robledo (10) Patent No.: US 12,298,129 B2
(45) Date of Patent: May 13, 2025

(54) OPTICAL COHERENCE TOMOGRAPHY SYSTEM FOR OPHTHALMOLOGY

(71) Applicant: Haag-Streit AG, Köniz (CH)

(72) Inventor: Lucio Robledo, Bern (CH)

(73) Assignee: Haag-Streit AG, Köniz (CH)

( * ) Notice: Subject to any disclaimer, the term of this patent is extended or adjusted under 35 U.S.C. 154(b) by 172 days.

(21) Appl. No.: 17/791,366

(22) PCT Filed: Jan. 8, 2020

(86) PCT No.: PCT/EP2020/050261
§ 371 (c)(1),
(2) Date: Jul. 7, 2022

(87) PCT Pub. No.: WO2021/139882
PCT Pub. Date: Jul. 15, 2021

(65) Prior Publication Data
US 2023/0035499 A1 Feb. 2, 2023

(51) Int. Cl.
*G01B 9/02* (2022.01)
*A61B 3/10* (2006.01)
*A61B 3/107* (2006.01)

(52) U.S. Cl.
CPC ............. *G01B 9/02* (2013.01); *A61B 3/102* (2013.01); *A61B 3/107* (2013.01)

(58) Field of Classification Search
CPC ............ G01B 9/02; A61B 3/102; A61B 3/107
See application file for complete search history.

(56) References Cited

U.S. PATENT DOCUMENTS

| | | | |
|---|---|---|---|
| 7,072,047 B2 | 7/2006 | Westphal et al. | |
| 7,452,077 B2 | 11/2008 | Meyer et al. | |
| 8,690,328 B1 | 4/2014 | Chong | |
| 8,705,048 B2 | 4/2014 | Everett et al. | |

(Continued)

FOREIGN PATENT DOCUMENTS

| | | |
|---|---|---|
| CN | 109155058 | 1/2019 |
| CN | 110473265 | 11/2019 |

(Continued)

OTHER PUBLICATIONS

Japan Office Action conducted in counterpart Japan Appln. No. 2022-542054 (Jan. 9, 2024).

(Continued)

*Primary Examiner* — Jamil Ahmed
(74) *Attorney, Agent, or Firm* — GREENBLUM & BERNSTEIN, P.L.C.

(57) ABSTRACT

Data representing structures in an eye, in particular data for a cross-sectional image, is recorded by generating a plurality of A-scans using swept-source OCT at different locations in the eye, each of which generates a plurality of reflection values for a plurality of points along a light trace. Combined values are then calculated from several reflection values at different locations in the eye. For improving data quality, a model of at one curved structure in the eye is fitted to the reflection values, and it is then used for identifying the points on the A-scans that are to be combined. This allows to project the data along a tangential direction of the curved structures for reducing noise and for obtaining improved resolution in the direction perpendicular to the structure.

21 Claims, 7 Drawing Sheets

(56) References Cited

U.S. PATENT DOCUMENTS

| | | |
|---|---|---|
| 2007/0216909 A1 | 9/2007 | Everette et al. |
| 2012/0063660 A1* | 3/2012 | Imamura ............... A61B 5/0066 382/131 |
| 2014/0211154 A1 | 7/2014 | Artal Soriano et al. |
| 2016/0128565 A1 | 5/2016 | Meznaric et al. |
| 2017/0258318 A1 | 9/2017 | Wagner et al. |
| 2017/0358077 A1 | 12/2017 | Xu et al. |
| 2019/0034777 A1 | 11/2019 | Fleming et al. |
| 2020/0027227 A1 | 1/2020 | Holmes |
| 2021/0199420 A1* | 7/2021 | Stalder ............... G01B 9/02059 |

FOREIGN PATENT DOCUMENTS

| | | | |
|---|---|---|---|
| EP | 3021071 | 5/2016 | |
| EP | 3217144 | 9/2017 | |
| EP | 3 572 765 | 11/2019 | |
| EP | 3572765 A1 * | 11/2019 | ............ A61B 3/102 |
| JP | 2015-504740 | 2/2015 | |
| JP | 2016-202900 | 12/2016 | |
| JP | 2017-104309 | 6/2017 | |
| JP | 2018-043085 | 3/2018 | |
| WO | 2013/107649 | 7/2013 | |

OTHER PUBLICATIONS

Silke Aumann et al., "Optical Coherence Tomography (OCT): Principle and Technical Realization : New Frontiers in Biomedical Optics", In: "High Resolution Imaging in Microscopy and Ophthalmology: New Frontiers in Biomedical Optics ", Springer International Publishing, Cham, XP055735902, ISBN: 978-3-030-16638-0, Jan. 1, 2019, pp. 59-85.

Gangjun Liu et al., " A comparison of Doppler optical coherence tomography methods", Biomed Opt Express., vol. 3, No. 10, XP055745504, Sep. 26, 2012, pp. 2669-2680.

Dae Yu Kim et al., "In vivo volumetric imaging of human retinal circulation with phase-variance optical coherence tomography", Biomedical Optics Express, vol. 2, No. 6, XP055291698, ISSN: 2156-7085,, May 11, 2011, pp. 1504-1513.

Florian Beer et al., "Conical scan pattern for enhanced visualization of the human cornea using polarization-sensitive OCT", Biomedical Optics Express 2906, vol. 8, No. 6, Jun. 1, 2017, PP.

Ireneusz Grulkowski et al., "Volumetrie macro- and micro-scale assessment of crystalline lens opacities in cataract patients using long-depth-range swept source optical coherence tomography", Biomedical Optics Express 3821, vol. 9, No. 8 , Aug. 1, 2018, PP.

Meixiao Shen et al., "SD-OCT With Prolonged Scan Depth for Imaging the Anterior Segment of the Eye", Ophthalmic Surgery, Lasers & imaging · vol. 41, No. 6 , Apr. 16, 2010, pp. S65-69.

Ali Tabatabaei et al., "Evaluation of Posterior Lens Capsule by 20-MHz Ultrasound Probe in Traumatic Cataract", Farabi Eye Hospital, Eye Research Center, Tehran University of Medical Sciences, Tehran, Iran, May 22, 2011, pp. 51-54.

Int'l Search Report (Form PCT/ISA/210) conducted in Int'l Appln. No. PCT/EP2020/050261 (Nov. 10, 2020).

Int'l Written Report (Form PCT/ISA/237) conducted in Int'l Appln. No. PCT/EP2020/050261 (Nov. 10, 2020).

Int'l Prelim. Exam. Report (Form PCT/IPEA/409) conducted in Int'l Appln. No. PCT/EP2020/050261 (Apr. 13, 2022).

China Search Report/Office Action conducted in counterpart China Appln. No. 202080093820.3 (Oct. 23, 2024).

Japan Office Action (JP OA) conducted in counterpart Japan Appln. No. 2024-074346 (Mar. 4, 2025).

* cited by examiner

OPTICAL COHERENCE TOMOGRAPHY SYSTEM FOR OPHTHALMOLOGY

TECHNICAL FIELD

The invention relates to a method for obtaining data representing structures in an eye as well as to an ophthalmologic device for carrying out this method.

BACKGROUND ART

Optical coherence tomography (OCT) systems for ophthalmologic applications have e.g. be known from EP 3572765. They comprise an optical coherence tomography interferometer. This interferometer is used for recording a plurality of A-scans of the eye. Each A-scan consists of a series of reflection values for a plurality of points along a light trace through the eye. These reflection values can then e.g. be used to generate images of the eye in either one, two, or three dimensions.

DISCLOSURE OF THE INVENTION

The problem to be solved by the present invention is to provide a method and device of the type mentioned above that yield data with more information, e.g. with better resolution and/or less noise.

This problem is solved by the method and device of the independent claims.

Accordingly, the invention relates to a method for obtaining data representing structures in an eye, in particular data representative of a cross-sectional image, by means of optical coherence tomography.

The data obtained by the present technique may e.g. represent a one-dimensional or two-dimensional cross-section of the eye and/or individual parameters of the eye.

The method comprises at least the following steps:

Recording a set of A-scans: At least some of these A-scans are recorded at different locations of the eye. Each A-scan is used to generate a plurality of reflection values e.g. as a function of the optical penetration depth in the eye.

Calculating a plurality of combined values. Each such combined value is obtained from reflection values at different locations in the eye.

By combining reflection values obtained at different locations in the eye into said "combined values", additional or more accurate information can be gained as described below.

Advantageously, the method further comprises the step of using the reflection values for modelling at least one curved structure of the eye. This curved structure may be any structure that is discernable from the reflection values, such as the anterior or posterior surface of the cornea or of the lens or the retina.

Advantageously, the modeled curved structure can be used for identifying the points on a subset of the A-scans that are to be used for calculating a given combined value. This allows to e.g. "project" the data of the A-scans along a tangential direction of the curved structure when combining the reflection values into a combined value, thereby improving the spatial resolution in a direction perpendicular to the direction of the curved structure and/or improving the signal-to-noise ratio of the data.

The subset of used A-scans advantageously comprises several A-scans recorded at different locations in the eye.

For calculating a combined value at the curved structure, the method may advantageously comprise at least the following steps:

In the subgroup of the A-scans to be used, determining, for each A-scan i, an estimate $r_e(i)$ of the reflection value at the intersection of the A-scan i with the modeled structure. This estimate can e.g. be the reflection value of the measured point on A-scan i that is closest to the intersection, or it may be an interpolation value of the reflection values of the A-scan i at the location of the intersection.

Using the estimates $r_e(i)$ for calculating the combined value. In one embodiment, for calculating the combined values along a given axis, the method may further comprise the following step:

Using the reflection values for modelling at least a first and a second curved structure in the eye, with the first structure being located at a first position along the axis and the second structure being located at a second, different position along the axis. For example, the first structure may be the anterior surface of the lens (or cornea), and the second structure may be the posterior surface of the lens (or cornea).

In that case, advantageously, the method may comprise at least one of the following two steps:

For obtaining the combined value at the first position, combining a first plurality of the reflection values from different A-scans of points tangentially along the first curved structure. In the example above, this would mean that reflection values tangentially along the anterior surface of the lens are combined to generate the combined value at the position where the axis intersects the anterior surface.

For obtaining a combined value at the second position, combining a second plurality of the reflection values from different A-scans of points tangentially along the second curved structure. In the example above, this would mean that reflection values tangentially along the posterior surface of the lens are combined to generate the combined value at the position where the axis intersects the posterior surface.

Since the first and the second structures are different structures, the geometries for combining reflection values at the first and second position will therefore follow different curves within the eye, each one optimized for the respective structure to be represented.

In order to obtain a combined value at a third position between the first and the second position, the method may also comprise the step of obtaining a combined value at a third position between said first and said second position. This is achieved by combining a third plurality of the reflection values of points from different A-scans, with these points being in a region between and/or in the vicinity of the first and the second structure. In this context, "in the vicinity" is advantageously understood as designating points that have a distance of less than 500 μm, in particular of less than 100 μm, in particular of less than 10 μm, from the respective structure.

When the data represents a two-dimensional cross-section of the eye, it can be used to show an image of the structure that has been modeled, such as a cross-section of the cornea or lens. In that case, the combined values calculated by combining a plurality of the reflection values tangentially along the structure can be used for generating image points of the structure in the sectional view.

Advantageously, the combined values are calculated by combining a plurality of the reflection values from different A-scans outside the plane of the two-dimensional cross-section.

As mentioned, the "combined values" are calculated by combining reflection values of different A-scans. This operation may comprise at least one of the following operations:

calculating an average, in particular a weighted average, of the reflection values to be combined, calculating a quantile, in particular a median, of the reflection values to be combined, calculating a minimum or maximum of the reflection values to be combined, and/or calculating an interpolation of the reflection values to be combined.

When calculating the combined values, reflection values of A-scans exhibiting specular reflection are advantageously not used. Rather, neighboring A-scans that do not exhibit specular reflection can be used. In this context, an A-scan "exhibiting specular reflection" is to be understood as an A-scan that has reflection values originating from specular reflection recorded by the OCT measurement.

The present method allows to suppress such specularly reflecting A-scans because it can rely on the combination of neighboring A-scans.

Color can be used to provide additional information on the structure of the eye. For example, the "data" calculated by the present method may represent a two-dimensional image in an image plane, and the "combined values" may be color values attributed to pixels in the image. The method then may comprise at least the following steps:

Identifying, for each pixel, at least one reflection value at a point corresponding to the pixel.

Determining the color for the pixel, with the color depending on the distance of the point from the image plane.

This allows to attribute different colors depending on the location of a reflecting structure in respect to the cross-sectional image.

The invention also relates to an ophthalmologic device comprising

An optical coherence tomography interferometer: This OCT interferometer is used to record the A-scans.

A control unit structured and adapted to carry out the method described herein: This control unit is provided with suitable software and hardware for carrying out the steps of the invention. It may also comprise a display, storage, and/or data interface for displaying, storing, and/or transferring the data determined by the present techniques.

BRIEF DESCRIPTION OF THE DRAWINGS

The invention will be better understood and objects other than those set forth above will become apparent when consideration is given to the following detailed description thereof. Such description makes reference to the annexed drawings, wherein.

(Note: All grayscale images in the figures have been half-toned for better reproducibility. Half-toning is typically not used when representing the images on an electronic display.)

MODES FOR CARRYING OUT THE INVENTION

Device Overview

Figure 1:
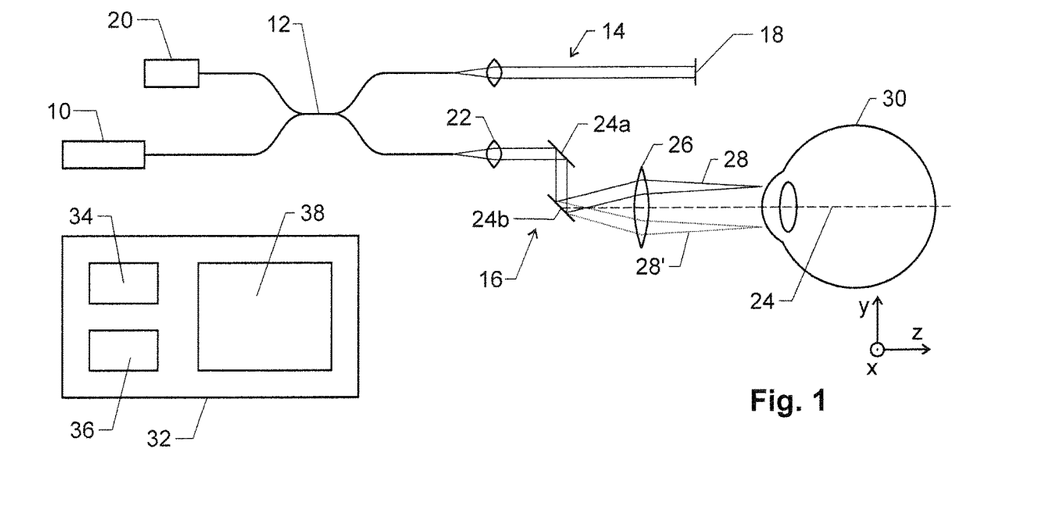
FIG. 1 shows the schematic setup of an embodiment of an ophthalmologic device.

The ophthalmologic device of FIG. 1 is e.g. an ophthalmologic microscope with OCT capability.

It comprises an optical coherence tomography interferometer 10-26.

The interferometer has a light source 10, which, in the present embodiment, is a swept-source light source, i.e. it generates narrowband light that can be adjusted in wavelength.

The light from light source 10 passes a beam splitter 12, in particular a fiber beam splitter, and is sent into two interferometer arms 14, 16.

The first arm is the reference arm 14, which comprises a mirror 18 at one end. Light impinging on mirror 18 is sent back into beam splitter 12 and from there, at least in part, to a light detector 20.

The second arm is the sample arm 16. It comprises collimation optics 22 for collimating the probe light coming from beam splitter 12. The light is then fed through two scanner mirrors 24a, 24b and an objective lens 26 for generating a probe beam 28. Depending on the position of the scanner mirrors 24a, 24b, probe beam 28 can be laterally offset in an x-y-plane perpendicular to the optical axis z of the device.

In the present embodiment, an interferometer generating telecentric probe beams 28 is used, i.e. the probe beams 28 for various x- and y-coordinates (such as beam 28 and beam 28' in FIG. 1) are parallel to each other. This simplifies the analysis in the context of the techniques described below.

In the shown embodiment, the probe beams are shown to be focused on the anterior surface of the cornea, but they may also be focused on any other part of the eye 30 that is of particular interest.

Probe beam 28 enters eye 30, where it is reflected or scattered by the structures of the eye. Light cast back from such structures is returned to beam splitter 12 and from there, at least in part, to light detector 20, where it can interfere with the light from reference arm 14.

The device of FIG. 1 is operated by recording a plurality of A-scans. For each such A-scan, probe beam 28 is brought into a desired x- and y-position by means of the scanner mirrors 24a, 24b. Then, the central wavelength of light source 10 is tuned over a given wavelength range, which wavelength range is typically much broader than the spectral width of the light from light source 10. The light at light detector 20 is measured as a function of the central wavelength.

Spectral analysis, in particular a Fourier transform, of the signal from detector 20 can then be used for generating the reflection values of eye 30 along axis z for the given A-scan. Reflection values are meant to relate to reflected and scattered light as described above. As customary in OCT imaging, reflection values might be represented by values proportional to the reflected intensity or by values proportional to a logarithm of the reflected intensity or e.g. by other range-compressed values. In more general terms, a "reflection value" is indicative of the amount of light returned from a certain position along an A-scan. Advantageously, it may be linear to the amount of light or a logarithm thereof or any other function thereof.

This type of OCT measurement is known to the skilled person, and it is e.g. described in EP 3572765 and the references cited therein.

The device further comprises a control unit 32, which may e.g. be provided with a microprocessor 34 and with a memory 36 as well as with a display 38. Memory 36 may hold the data as well as the program instructions required for carrying out the steps of the present method. Display 38 may e.g. be used for showing the data determined thereby and in particular for displaying any cross-sectional images derived by means of the techniques described herein.

Advantageously, the measuring range (for a single A-scan) of the OCT interferometer 10-26 extends at least from the cornea to the retina of a typical eye. In other words, with a single A-scan (i.e. for an SS-OCT with a single sweep of the light source), depth-resolved information over at least 40 mm (in air) can be obtained. This allows to apply the techniques described in the following to be used over the whole axial eye length without the need to e.g. apply stitching for combining different measurements.

Figure 2:
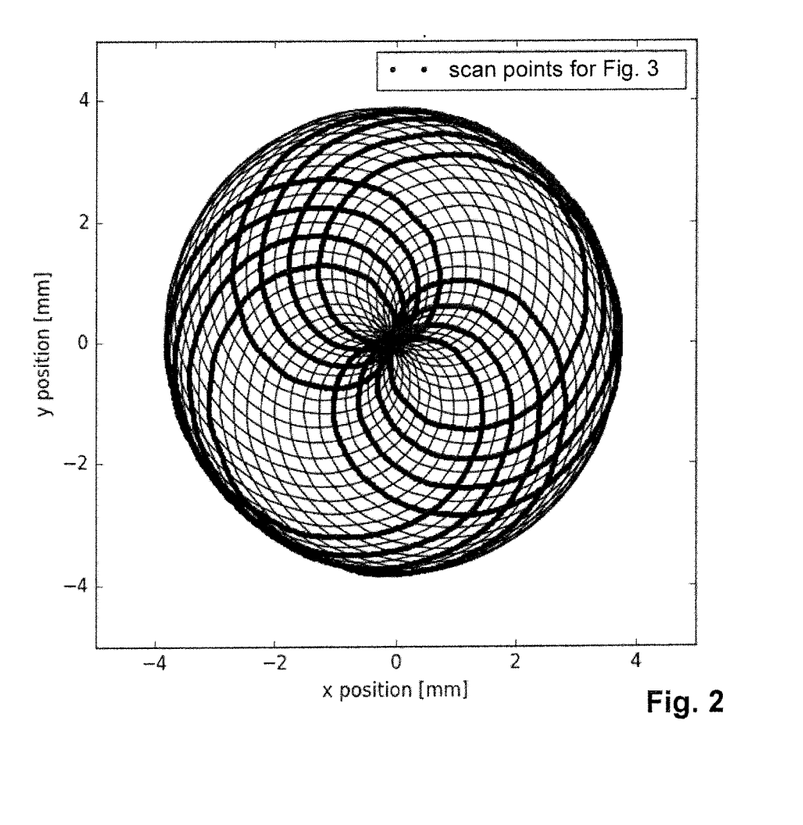
FIG. 2 shows an embodiment of a scan pattern.

FIG. 2 shows an example for a scan pattern used in the measurement, i.e. it shows the locations of the probe beam 38 in the x-y-plane during the various A-scans. This type of pattern is described in EP 3021071. Other scan patterns can be used as well, such as the scan patterns e.g. described in EP 3217144 or U.S. Pat. No. 8,705,048.

Figure 3:
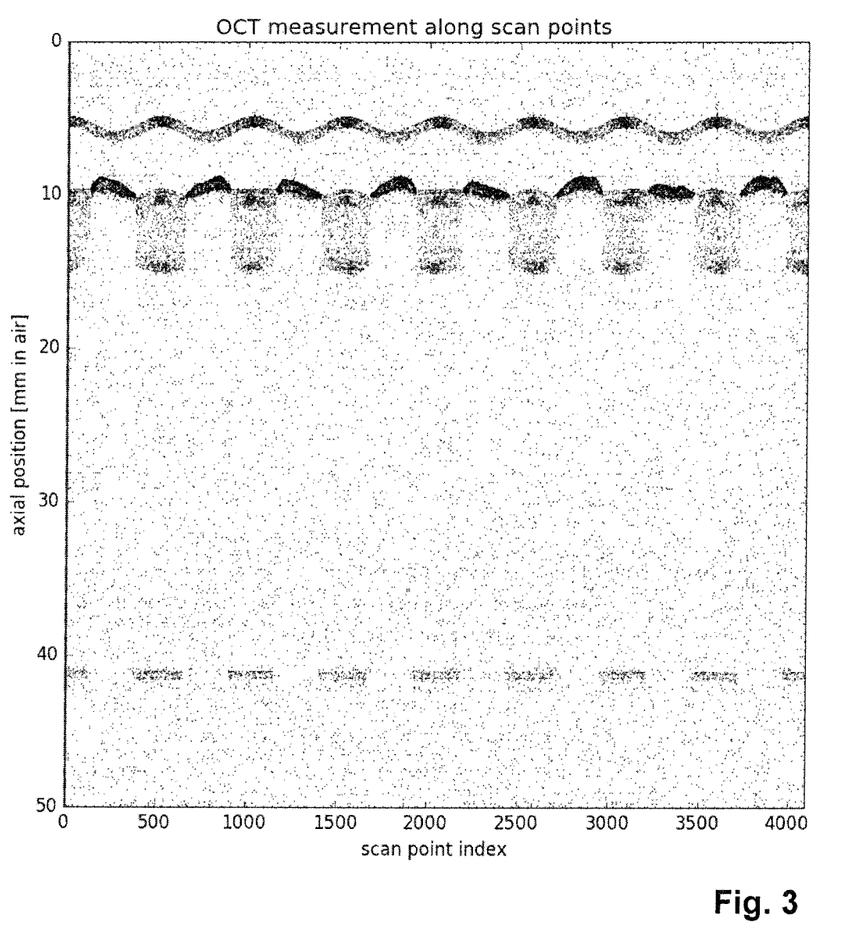
FIG. 3 shows the reflection values for the A-scan locations shown in bold lines in FIG. 2.

FIG. 3 shows the reflection values r (raw data) as a function of the scan point index and the z-coordinate for the fat scan points shown in FIG. 2. In this drawing, higher reflection values are represented by darker spots. As it can be seen, this data is fairly noisy.

Eye Motion Correction

The A-scans recorded in this manner can optionally be corrected for eye motion, e.g. by using at least the following steps:

1. Identifying reflections of at least one given eye-structure (such as the anterior corneal surface) in the A-scans.
2. Fitting a model descriptive of the shape of the structure and of the motion of the structure to the locations of the identified reflections. This model can e.g. have geometric parameters (such as the curvature) of the structure as well as motion parameters (such as the three-dimensional location and velocity in x-, y-, and z-coordinates).

The parameters obtained in the fitting step 2 can then be used for translating the OCT measurements into a coordinate system that is fixed with the frame of the eye.

Suitable motion correction techniques are e.g. described in WO 2013/107649 or U.S. Pat. No. 7,452,077.

Combining A-Scans

The steps described above generate a set of A-scans recorded at different x-y-locations in the eye. Each A-scan comprises a plurality of reflection values $r(z_{ij})$ along a light trace in the eye, where i is the index of the A-scan (identifying the x- and y-position of the A-scan) and $z_{ji} \ldots z_{iN}$ designate the z-locations along the depth of the eye as recorded in A-scan i.

As mentioned, the reflection values $r(z_{ij})$ are advantageously, but not necessarily, motion-corrected.

The present technique is based on obtaining data describing the structures of the eye. The data may e.g. represent a one-dimensional or two-dimensional cross section of the eye, or it can e.g. also represent a three-dimensional volumetric image of the eye.

In order to calculate the data representing the eye at a given location, the present technique calculates "combined values" $r_e$, where at least some of these combined values are each obtained from several reflection values $r(z_{ij})$ recorded for different locations of the eye.

In the following, some methods for calculating such combined values are are described.

Projections Along Eye Structures

One of the techniques described here is based on modelling at least one curved structure of the eye and then combining reflection values of different A-scans tangentially along this curved structure.

Figure 4:
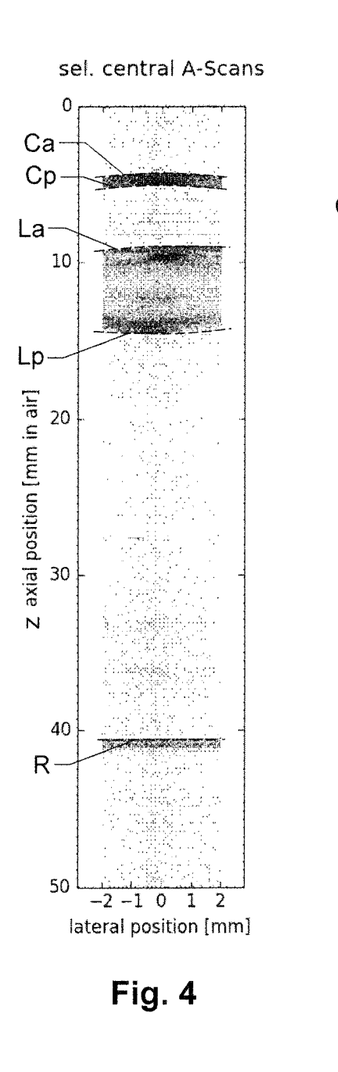
FIG. 4 represents a series of A-Scans in a plane.

This is illustrated in FIG. 4, which represents a series of A-scans in a plane. The image clearly shows the anterior and posterior surfaces Ca, Cp of the cornea as well as the anterior and posterior surfaces La, Lp of the lens. It also shows the retina R. (Since—for telecentric A-scans extending (outside the eye) parallel to the eye's visual or optical axis, the A-scans intersect in one point of the retina, the retina appears at substantially the same z-coordinate for all A-scans.)

Using e.g. edge detection techniques on each A-scan, the z-position (axial position along the light trace) of any of these surfaces can be estimated in order to obtain e.g. four sets of points in x-y-z-space corresponding to each one of these surfaces.

In a next step, the parameters of a model of each one of these surfaces can be can be calculated e.g. using conventional fitting techniques.

For example, the surfaces can be modeled by spherical surfaces defined by a center and a radius, or they can be modeled by polynomial surfaces of e.g. second degree.

Once the parameters of the models have been calculated, a refined "combined value" at on one of the surfaces for given x-y-coordinates can be calculated, namely by projecting the reflection values of several A-scans along said surface and combining them mathematically, e.g. by averaging or by another mathematical operation as described further below.

Figure 5:
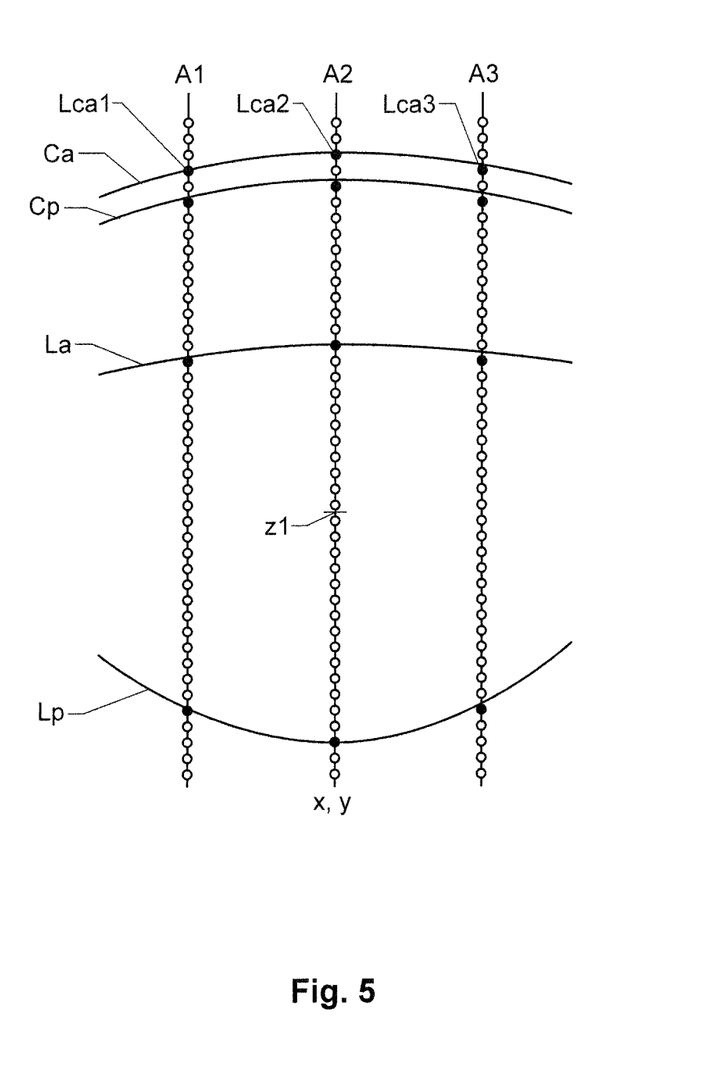
FIG. 5 is a schematic representation of three A-scans and of the anterior and posterior surfaces of the cornea and the lens.

This process is illustrated schematically in FIG. 5, which shows three A-scans A1, A2, A3 as well as the four surfaces Ca, Cp, La, and Lp as obtained by fitting. The dots/circles along the A-scans represent the z-positions $z_{ji}$ at which reflection values $r(z_{ij})$ have been measured.

In order to e.g. obtain a refined, combined reflection value $r_c$ at the intersection of the surface Ca with A-scan A2, the reflection values of the three A-scans A1, A2, A3 along surface Ca can be combined.

A simple algorithm may e.g. identify, for each A-scan, the measurement location (i.e. z-location) LCa1, LCa2, LCa3 closest to surface Ca and combine their reflection values r(LCa1), r(LCa2), r(LCa3).

A more refined algorithm may not only identify the locations LCa1, LCa2, LCa3 closest to surface Ca but e.g. also the second closest locations and interpolate, for each A-scan, the reflection values of these closest locations in order to obtain a better estimate of the reflection value at the intersection of the A-scan with surface Ca and then mathematically combine these estimates.

In more general terms, in order to estimate the reflection value $r_c$ at a given location x, y on a structure (such as one of the surfaces Ca, Cp, La, Lp) of the eye, the following steps can be carried out:

Step 1 (modelling). Model at least one curved structure of the eye to the reflection values measured by the A-scans. For this modelling step, only the subset of A-scans of step 2 below may be used, or a larger set of A-scans may be used.

Step 2 (subset selection): Select a subset of the A-scans around the location (axis) x, y, for calculating a combined value $r_e$. This subset contains A-scans that are close to x, y, e.g. A-scans with a distance smaller than a value R from x, y. If R is chosen to be large, noise suppression is improved, but the resolution in x- and y-suffers. If R is chosen to be small, the noise will increase but the resolution is improved. Typically, R may e.g. be 1 mm or 0.5 mm.

Step 3 (determine individual A-scan reflection estimates): Calculate, for each A-scan i in the subset, an estimate $r_e(i)$ of the reflection value at the intersection of the A-scan with the modeled structure. This step may, for example, comprise the calculation of the intersection point of the A-scan i with the model structure and then e.g. using the measured reflection value for the closest to the intersection point as an estimate $r_e(i)$. Or it may comprise calculating an interpolated value of reflection values of the A-scan at the intersection point (which, indirectly, will also at least use the reflection value at the scan location closest to the intersection point as well as at least one further reflection value).

4. Combining the estimates $r_e(i)$ of the A-scans i in the subset into the combined value $r_e$. This combination can use various mathematical operations, which will be described in more detail below.

The steps above describe how to calculate the combined value $r_e$ at a given eye structure. These steps can be generalized to estimate the reflection value $r_e$ at any given location x, y, z, also away from any structure of the eye, e.g. at the location x, y, z1 of FIG. 5.

Figure 6:
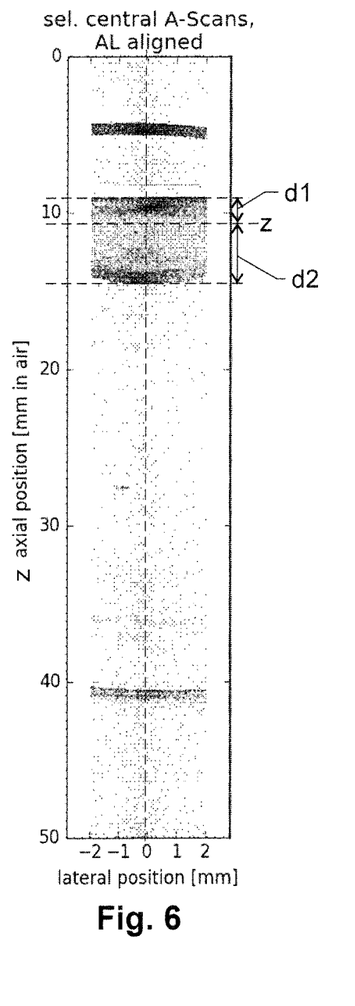
FIG. 6 shows the image of FIG. 4 with the A-scans displaced along the z-direction in order to set the anterior lens surface onto a single line.
Figure 7:
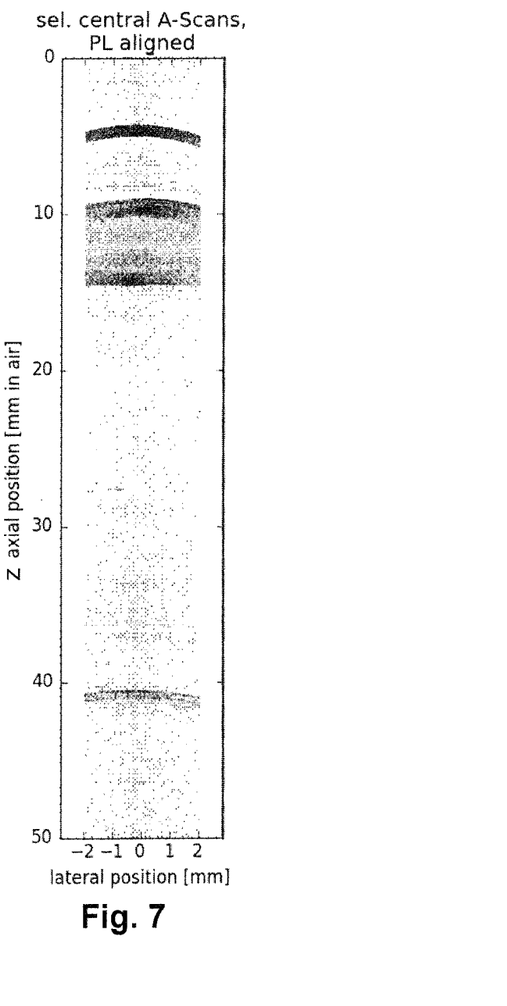
FIG. 7 shows the image of FIG. 4 with the A-scans displaced along the z-direction in order to set the posterior lens surface onto a single line.

A first method is illustrated in FIGS. 6 and 7.

FIG. 6 shows the A-scans of FIG. 4, but each A-scan has been offset along direction z such that their reflection peaks corresponding to anterior surface La of the lens are at the same z-positions. Similarly, FIG. 7 shows the A-scans of FIG. 4, but each A-scan has been offset along direction z such that their reflection peaks corresponding to anterior surface Lp of the lens are at the same z-positions.

In that case, for calculating a combined value $r_c(z)$ at a given z-position between the anterior and posterior surfaces La, Lp of the lens, the estimate $r_e(i)$ for a given A-scan i can e.g. be the weighted average of the reflection value $r'(i, z)$ of A-scan i of FIG. 6 and the reflection value $r''(i, z)$ A-scan i of FIG. 7. The weights are chosen linearly depending on the distances d1, d2 of point z from La and Lp, respectively, with a distance, i.e.

$$r_e(z) = (d1 \cdot r''(i,z) + d2 \cdot r'(i,z))/(d1+d2). \quad (1)$$

In other words, two sets of an A-scans are calculated by offsetting the A-scans along z, with the first set being aligned at the first structure and the second set being aligned at the second structure. Then, in order to calculate the estimate $r_e(i)$ for a given A-scan i at a given location z between these structures, the reflection values r' and r'' of the A-scan i in the two sets are combined using Eq. (1).

Figure 8:
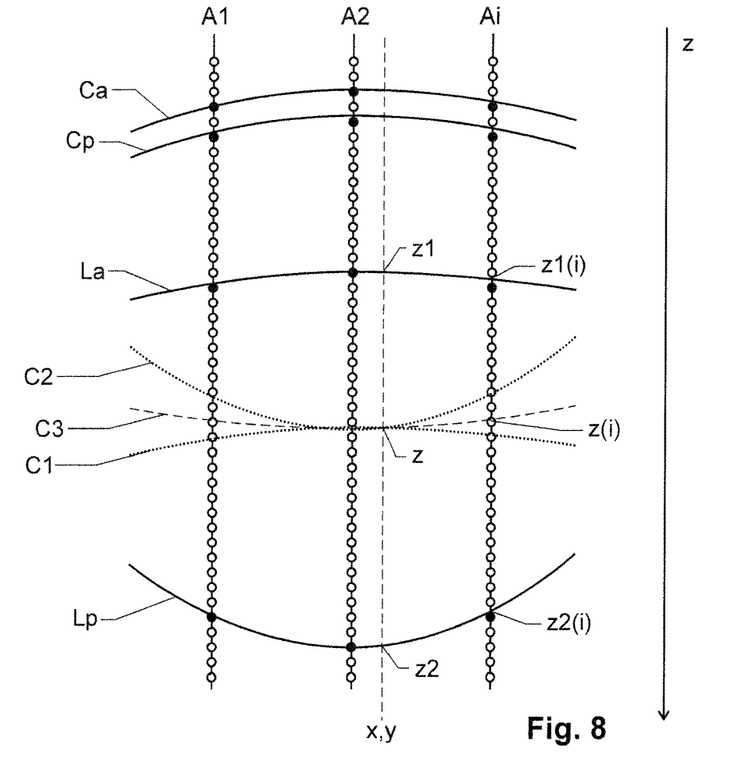
FIG. 8 is a schematic representation of one embodiment to determine the estimate to be used for an A-scan i when calculating the combined value at a location x, y, z.

A second method is illustrated in FIG. 8. Here it is assumed that the combined value for a given location x, y, z is to be calculated from a subset of A-scans close to x, y, z. The figure illustrates what location z(i) along A-scan i (denoted as Ai) is to be used. Namely, the estimate $r_e(i)$ to be used for A-scan i is determined as follows:

The z-positions z1 and z2 of two eye-structures (here the structures La and Lp) at the location x, y are calculated, as well as at the z-positions z1(i) and z2(i) of the two eye-structures at the x-y-location of A-scan i.

A location z(i) on A-scan i is calculated from z1 and z2, z1(i), and z2(i), which takes into consideration that z(i) should be between z1(i), and z2(i) in a manner similar to z being between z1 and z2. For example, the following relation can be used to calculate z(i):

$$z(i) = z1(i) + (z2(i) - z1(i))(z - z1)/(z2 - z1). \quad (2)$$

Then, the estimate $r_e(i)$ at location z(i) can be calculated. For example, it can be calculated using the reflection value of A-scan i at the measured point closest to z(i), or it can be calculated from an interpolation of the reflection values of A-scan i at the location z(i).

In more general terms, for calculating the combined value at a position z between the positions z1 and z2, the method may combine a "third plurality" of the reflection values (r) of A-scan-points located in the region between and/or in the vicinity of the two modeled structures of the eye. As mentioned above, "in the vicinity" is advantageously understood as designating points that have a distance of less than 500 μm, in particular of less than 100 μm particular of less than 10 μm, from the respective structure. The case "in the vicinity" may e.g. apply when using the technique as defined under b) below, in which case some of the "third plurality" of values may lie outside the two modeled structures. (Such structures may have a typical curvature radius of 8 mm or more, and the distance of the points corresponding to the third plurality of reflection values may be up to almost 3 mm, probably less, which results in the maximum definition of the "vicinity" of 500 μm.)

The "third plurality" can e.g. be defined in one of the following manners:

a) When using the technique of Eq. (1), this "third plurality" of reflection values can e.g. be defined as comprising the reflection values of a first and a second subset of points on the used A-scans:

The points of the first subset are arranged tangentially along a first (advantageously three-dimensional) curve C1 parallel to the first modeled structure (La in FIG. 8), and this first curve is offset to intersect the point at coordinates x, y, z.

The points of the second subset are arranged tangentially along a second (advantageously three-dimensional) curve C2 parallel to the second modeled structure (Lp in FIG. 8), and this second curve is also offset to intersect the point at coordinates x, y, z.

In other words, the first and second curves C1, C2 intersect at point z.

b) When using the technique of Eq. (2), the "third plurality" of reflection values can e.g. be defined as reflection values for points on the used A-scans that extend tangentially along a curve C3 (advantageously three-dimensional curve) interpolated from the first and the second modeled structure (La, Lp in FIG. 8).

The techniques described in this section "Projections Along Eye Structures" are particularly advantageous for calculating combined values $r_e$ at x-y-positions away from the eye's vertex or visual or optical axis and/or for calculating combinations on geometrically wide subsets of A-scans, i.e. for large values of R because, in these cases, the curvature and/or slope of the structures would otherwise introduce large errors when calculating the combined value.

Calculating the Combined Value

Once that the estimates $r_e(i)$ of all the A-scans i in the subset of A-scans has been determined, the combined value $r_e$ at a location x, y, z can be evaluated. As mentioned above, the combined value $r_e$ can e.g. be one of the following values:

An average of the estimates $r_e(i)$ of the individual A-scans. Advantageously, a weighted average is used, where the weight of a given estimate $r_e(i)$ depends on the distance of the A-scan i from location x, y, e.g. using a Gaussian weight.

A quantile, such as the median, of the estimates $r_e(i)$.

A minimum or maximum of the estimates $r_e(i)$.

An interpolation of the estimates $r_e(i)$, e.g. by fitting a first or second degree polynomial $r_c(x, y)$ through the estimates $r_e(i)$, using the x- and y-coordinates of the A-scans i as independent variables.

Advantageously, the device comprises a user interface allowing the user to choose how the estimates $r_e(i)$ are to be combined. When the user wants to display a quantile, the user may e.g. be able to select continuously or in graded manner a value between the minimum, median, and maximum.

Suppressing Specular Reflections Typically, A-scans close to the vertex of the eye show strong speculolar reflection that may tend to override the information gained from the other A-scans in the subset considered.

Hence, in one embodiment, reflection values of any A-scan exhibiting specular reflection may be suppressed when calculating the combined values. This can e.g. be achieved by not using any A-scans that have a distance smaller than a threshold Rs from the apex of the cornea, with Rs e.g. being 0.1 mm.

Cross-Section Calculation The techniques described above may e.g. be used to calculate one- or two-dimensional cross-sections of the eye.

A particularly interesting cross-section is e.g. the one-dimensional cross-section along the visual or optical axis of the eye, i.e. the central A-scan. It can e.g. be obtained by using the subset of all A-scans having a lateral distance of e.g. less than 1 mm from the vertex, optionally e.g. excluding any A-scans closer than 0.1 mm from the vertex in order to suppress specular reflection signals as described above.

Figure 9:
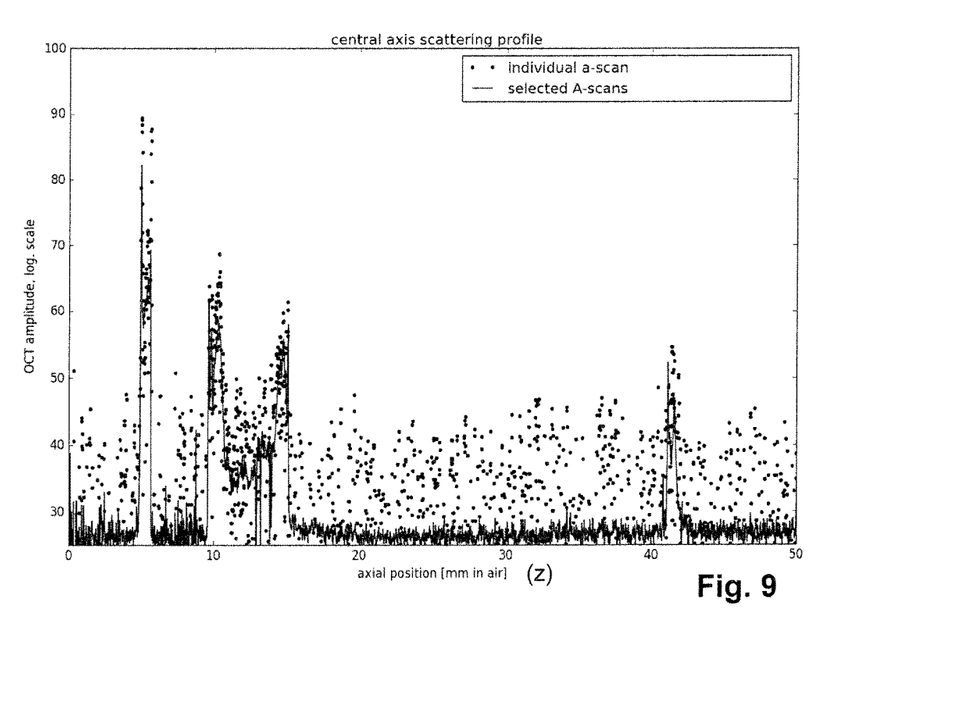
FIG. 9 represents the reflection values of a single A-scan and the combined values along the visual axis of the eye.

Such a cross-section, depicted as a graph of the combined value $r_c(z)$ is shown, as an example, in FIG. 9. The dots in this figure show an individual A-scan while the continuous line is the combined $r_c(z)$ value obtained by the method illustrated in FIGS. 6 and 7 for those A-scans of FIG. 3 with a distance between 0.1 and 1.0 mm from the vertex. As can be seen, the combined value $r_e$ has a noise much lower than the individual A-scan.

Figure 10:
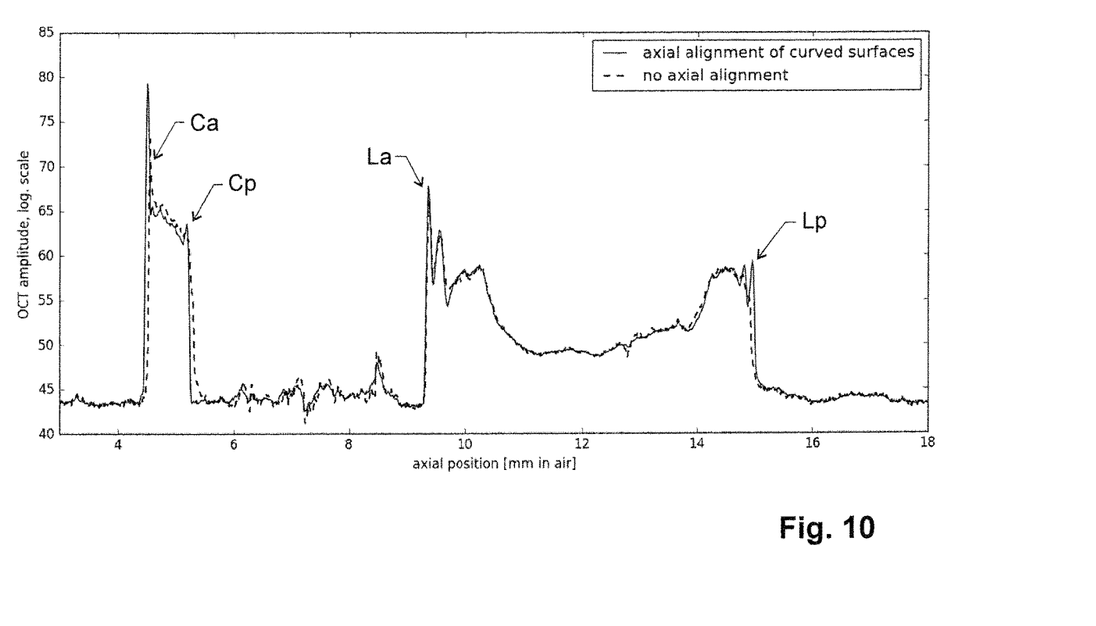
FIG. 10 represents combined values for a one-dimensional cross-section along the visual axis of the eye, zooming in on the cornea and lens and depicting the effects of projecting the individual A-scans along the surfaces of the cornea and lens.

FIG. 10 is another one-dimensional cross-section along the visual axis of the eye, only showing the eye's anterior section. The plot contains two curves:

The dotted curve shows the combined values $r_c(z)$ obtained from the A-scans in the subset without projecting the reflectivity values of the A-scans along the curved surfaces of the cornea and lens. Rather, the combined values $r_c(z)$ were obtained by just combining (e.g. by using the median) the respective values of the A-scans at the same z-coordinate (i.e. the A-scans in the subgroup were orthogonally projected onto the visual axis of the eye).

The solid curve shows the combined values $r_c(z)$ obtained from the A-scans in the subset using the projection technique along the curved surfaces and the combination using Eq. (1) above.

As can e.g. be seen for both surfaces of the cornea (points Ca and Cp in FIG. 10) as well as for the posterior surface of the lens (point Lp in FIG. 10), the solid curve reveals additional details and structures.

Further, the dotted line is offset to the right for the surfaces Ca, Cp, and La and offset to the left for surface Lp. This reflects the fact that the "orthogonal" projection generates systematic offset errors when being used at the apex of a surface. The corrected (solid) data does not show these errors.

The sectional data of FIGS. 9 and 10 can e.g. be used for measuring the depth of the cornea, the depth of eye's anterior chamber, the thickness of the lens, the total length of the eye, and/or dimensions of other structures of the eye, such as the thickness of the anterior lens capsular complex or of the corneal epithelium. The good S/N-ratio allows to obtain accurate results. Peak fitting can e.g. be used to localize the maxima of the individual scattering structures.

Further one-dimensional scans of this type can be obtained for points other than the eye's visual or optical axis, i.e. for arbitrary x-y-positions, and they can e.g. be used for generating a color-coded depth map of the corneal thickness, of the corneal epithelium thickness, and/or of the anterior chamber depth.

Several one-dimensional scans of this type can also be combined for generating two-dimensional cross-sectional data for cross-sectional planes parallel to the eye's visual or optical axis, e.g. for generating meridional cross-sectional images.

Two-dimensional cross-section data can be used for generating cross-sectional images, e.g. by encoding the combined values $r_c$ as gray-level values.

Advantageously, when generating such cross-sectional data, the combined values $r_c$ are calculated from the maximum of the reflection values of the corresponding locations of the A-scans in the used subgroup, even though the other techniques described in the section "Calculating the Combined Value" can be used as well.

Figure 11:
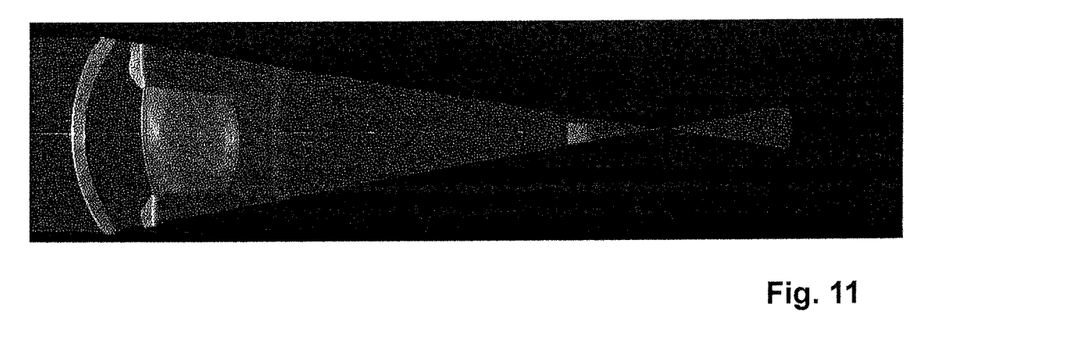
FIG. 11 shows a refraction-corrected cross-sectional image using the techniques described herein.

FIG. 11 shows such a (Jarvis-half-toned) cross-sectional image using averaging. The image has been refraction corrected, taking into account the refraction of the A-scans as they pass through the eye.

When generating two-dimensional cross-sectional data, the selection of the subgroup of A-scans to be combined can be asymmetric in respect to the cross-sectional plane. For example, when generating a horizontal cross-section (i.e. y=0), the combined values $r_c$ at a certain coordinate x0 can be calculated using a sub-group of A-scans within the area $x=x0\pm\Delta x$ and $y=\pm\Delta y$, with $\Delta y>\Delta x$, e.g. $\Delta y=2$ mm and $\Delta x=0.5$ mm.

In more general terms, when calculating cross-sectional data for a given cross-sectional plane, the subgroup of A-scans used for calculating the combined value $r_c$ at a given coordinate x, y, z only includes the A-scans within a volume of space that is larger in a direction perpendicular to the plane than in any direction parallel to the plane.

Depth Encoding

Yet another aspect of the invention relates to generating color-encoded images where color is used to encode the distance of structures from the image plane.

This method is, in the following, illustrated for an "en-face" image of the eye, i.e. an image representing the eye as seen from the front (i.e. as seen from the outside along direction z). However, it may also be used for generating any type of sectional images.

Without limiting the generality of the concept, the "image plane" for an image can be any plane perpendicular to the viewing direction.

In this aspect, similar as above, the method uses, for each point in the image, a subset of the A-scans or of the data points thereon and combines their reflection values for generating a combined value, which, in this case, is a color value.

Figure 12:
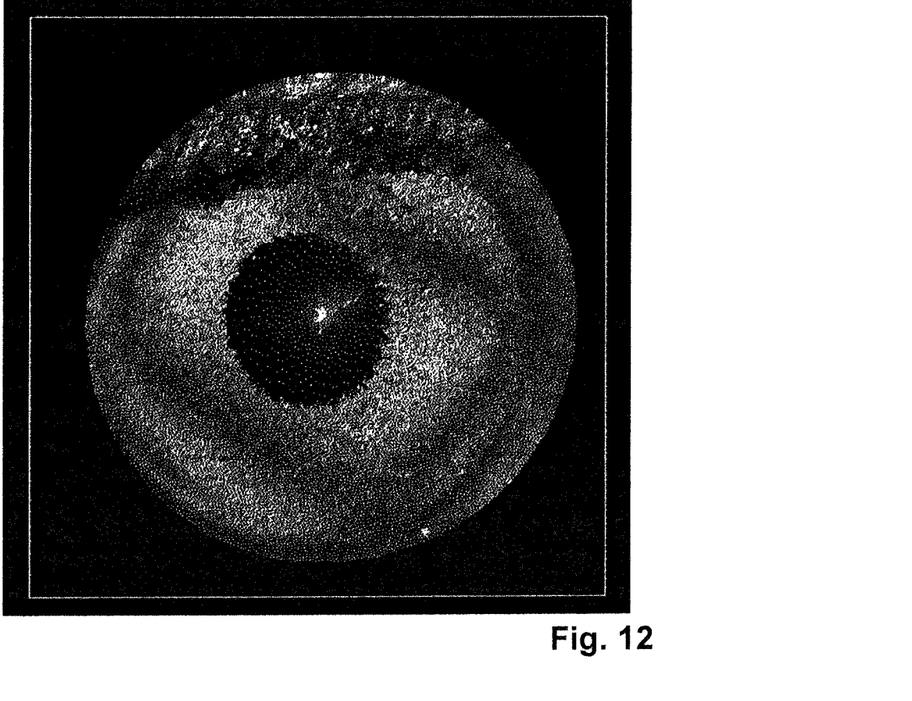
FIG. 12 shows the brightness values of the image of of an "en-face" view of the eye.
Figure 13:
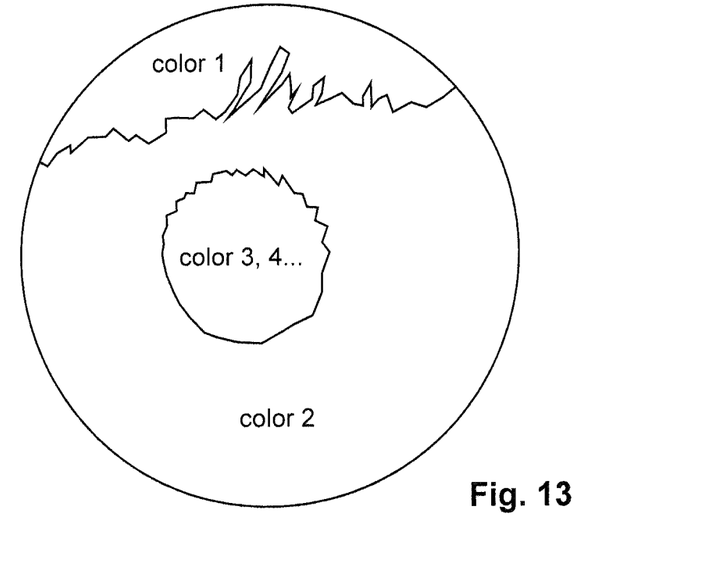
FIG. 13 shows the colors used for encoding various parts of the image of FIG. 13.

An example of a resulting en-face image is shown in FIGS. 12 and 13. In practice, i.e. as displayed on the electronic display 38 of the device, this image will be a color image. However, for representing it herein, FIG. 12 shows its gray-level (i.e. brightness or lightness), and FIG. 13 shows (in words) possible colors used in certain areas thereof.

This image, which is in the x-y-plane, i.e. perpendicular to the axes of the A-scans, can e.g. be calculated as follows:

1. Three two-dimensional arrays representing the pixels of the image are set up and initialized to zero. The first array D(m,n) stores distance values. The second array R(m,n) stores reflectivity values. The third array W(m,n) stores weight values.

2. For each A-scan i of interest, the following operations are carried out:

2a. Determine the z-position z(i) and amplitude r(i) of the largest reflection value on A-scan i.

2b. Iterate over at least a subset of the image pixels. For each image pixel m, n (corresponding to the position x(m), y(m) in the x-y-plane), a weight w is calculated, e.g.

$$w(m,n) = g(\sqrt{(x(m)-x(i))^2 + (y(m)-y(i))^2}, \sigma), \quad (4)$$

with x(i), y(i) being the center x- and y-coordinates of A-scan i and with g(r, a) being a Gaussian function with a given variance a. The variance a depends on the diameter of the A-scan i.

The weight w(m, n) is added to third array W(m,n). w(m, n)·z(i) is to added to the first array D(m,n). w(m, n)r(i) is added to the second array R(m,n).

3. Once that all (or a desired subset of the) A-scans i have been processed in this manner, the following operations are carried out for each pixel m, n of the image:

3a) An average reflectivity f(m,n) is determined e.g. using $$\bar{r}(m,n) = R(m,n)/(W(m,n)+\varepsilon), \quad (5)$$

with ε being a small number for avoiding a division by zero.

3b) An average depth d(m,n) is determined e.g. using $$\bar{d}(m,n) = D(m,n)/(W(m,n)+\varepsilon). \quad (6)$$

3c) The average depth $\bar{d}(m,n)$ is e.g. used for determining a color or hue. This can e.g. be implemented by means of a look-up table delivering a color as a function of the average depth. In RGB color space, this color may e.g. by represented by its RGB components.

3d) The average reflectivity $\bar{r}(m,n)$ is e.g. used to set the brightness of the color or hue. In RGB color space, this may e.g. be implemented by multiplying the RGB components by the average reflectivity and subsequently nonnalizing the RGB values.

The color by steps 3c and 3d manner is attributed to the pixel n, m. In the example of FIGS. 12 and 13, for example, the structures in the top part of the image are reflections from the eyelid. Since they are closest to the viewer, the will have a first color 1 (or range of colors). The reflections originating from the iris are further away from the viewer and will appear in a second color 2.

The reflections visible in the pupil may e.g. originate from reflections at the cornea, at the anterior lens surface, at the posterior lens surface, or at structures deeper within the eye. Depending on where they come from, they will carry different colors 3, 4, etc.

Hence, the image shown in FIGS. 12 and 13 allows to easily distinguish between different scattering structures in the eye.

The same technique can be exploited not only for an en-face view of the eye, but also for virtual views from other directions. In that case, step 2 above not carried out for the A-scans, but for e.g. cylindrical or prismatic regions extending perpendicular to the image plane.

Note: instead of using the average reflectivity, in the steps 3 above, the method may also use any other combination, such as using the maximum reflectivity and its depth.

Advantageously, the determination of the color (in step 3c above) involves comparing the average depth $\bar{d}(m,n)$ to the location of the modeled surfaces in the eye, i.e. the surfaces Ca, Cp, La, and Lp and the retina R, and attributing the color as a function depending on this determination. This allows to color the pixels depending on the structure the reflection originates from.

In more general terms, the "data" calculated by the present method may represent a two-dimensional image defining image plane, and the "combined values" may be color values attributed to pixels in the image. The method then comprises at least the following steps:

Identifying, for each pixel, at least one reflection value at a point corresponding to the pixel (e.g. because the point is in a space volume extending perpendicularly to the image and having a cross-section corresponding to the pixel, optionally taking into account refraction at interfaces of the eye).

Determining a color for the pixel, with the color depending on the distance of the point from the image plane.

Advantageously, for each pixel, the point with the strongest reflection value corresponding to the pixel is used when determining the color.

Further, the magnitude of the reflection value of the point(s) corresponding to a pixel may be used for determining the brightness or lightness of the pixel.

The step of determining the color of a pixel advantageously involves the following sub-steps:

Comparing said distance with the location of several structures Ca, Cp, La, Lp that have been modeled to the reflection values. This allows to perform an "attribution" of the point in one of the structures or to a space between, before or behind the structures. For example, a point may be attributed to the space in front of the cornea, to the cornea itself, to the space between the cornea and the lens, to the anterior surface of the lens, to the interior of the lens, to the posterior surface of the lens, to the space between the lens and the retina, or to the retina. Other attributions are possible, too, e.g. by more finely resolving the cornea (attributing a point to the anterior surface of the cornea, the interior of the cornea, or the posterior surface of the cornea) or by more coarsely resolving the lens (attributing a point to the lens as a whole).

Choosing the color depending on the this attribution.

This e.g. allows to attribute the same color to all reflections from a given structure even if this structure is curved in respect to the image plane.

Notes

The techniques described herein are particularly suited for determining data representative of a cross-section parallel to the visual or optical axis of the eye. This cross-section may be a one-dimensional cross-section, e.g. a linear cross-section along the visual or optical axis of the eye, or it may be a two-dimensional cross section, e.g. represented as a cross-sectional image.

In another embodiment, the data may be representative, as shown, of a two-dimensional cross-section or image perpendicular to the visual or optical axis of the eye.

However, the data may e.g. also be representative of other parts of the eye, e.g. of a single point of the eye, of the whole volume of the eye, or of certain parameters (such as eye length, etc., see the examples above.).

The techniques can be used for any kind of OCT, in particular for time-domain OCT as well as frequency-domain OCT. Frequency-domain OCT, and in particular swept-source OCT, is, however, advantageous for its ability to obtain an A-scan quickly.

While there are shown and described presently preferred embodiments of the invention, it is to be distinctly understood that the invention is not limited thereto but may be otherwise variously embodied and practiced within the scope of the following claims.

The invention claimed is:

1. A method for obtaining data representing structures in an eye, in particular data representative of a cross-sectional image, by optical coherence tomography, said method comprising:
   recording a set of A-scans, wherein at least some of said A-scans are recorded at different locations of the eye, and wherein each A-scan is used to generate a plurality of reflection values for a plurality of points along a light trace through the eye;
   calculating a plurality of combined values, wherein each combined value is obtained from several reflection values at different locations in said eye;
   using said reflection values for modelling at least one curved structure of the eye; and
   calculating a combined value at the curved structure by:
      determining, for each A-scan i in said subset, an estimate $r_e(i)$ of the reflection value at the intersection of the A-scan i with the modeled structure, and using the estimates $r_e(i)$ for calculating the combined value.

2. The method of claim 1, wherein said curved structure is one of an anterior surface of the cornea, a posterior surface of the cornea, an anterior surface of the lens, a posterior surface of the lens, and the retina.

3. The method of claim 1, comprising calculating said combined values along a given axis by:
   using said reflection values for modelling at least a first and a second curved structure in the eye, wherein said first curved structure is located at a first position along said axis and said second curved structure is located at a second position along said axis.

4. The method of claim 3, further comprising at least one of:
   for obtaining a combined value at the first position, combining a first plurality of the reflection values from different A-scans of points tangentially along said first curved structure, and/or
   for obtaining a combined value at the second position, combining a second plurality of the reflection values from different A-scans of points tangentially along said second curved structure.

5. The method of claim 1, wherein said data represents a two-dimensional cross-section showing a sectional view of said structure, said method comprising using the combined values for generating image points of the curved structure in the sectional view.

6. The method of claim 5, wherein, for at least some of the combined values, the combined value is calculated by combining a plurality of the reflection values from different A-scans outside a plane of the cross-section.

7. The method of claim 1, wherein the calculating of a plurality of combined values comprises at least one of
   calculating an average of the reflection values to be combined,
   calculating a quantile of the reflection values to be combined,
   calculating a minimum or maximum of the reflection values to be combined,
   calculating an interpolation of the reflection values to be combined.

8. The method of claim 1, wherein the locations of the reflection values used for combining a combined value are within a distance of less than 1 mm from said axis.

9. The method of claim 1, wherein said data is representative of a one-dimensional cross section of the eye.

10. The method of claim 1, wherein said data is representative of a one-dimensional or two-dimensional cross-section parallel to a visual or optical axis of the eye.

11. The method of claim 1, wherein said data is representative of a two-dimensional cross-section perpendicular to the visual or optical axis of the eye.

12. The method of claim 1, wherein said optical coherence tomography is Frequency-domain OCT.

13. The method of claim 1 being performed by an optical coherence tomography interferometer having a measurement range of at least 40 mm for a single A-scan.

14. The method of claim 1 being performed by an optical coherence tomography interferometer generating telecentric probe beams.

15. An ophthalmologic device comprising
   an optical coherence tomography interferometer, and
   a control unit structured and adapted to carry out the method of claim 1.

16. A method for obtaining data representing structures in an eye, in particular data representative of a cross-sectional image, by optical coherence tomography, said method comprising:
   recording a set of A-scans, wherein at least some of said A-scans are recorded at different locations of the eye, and wherein each A-scan is used to generate a plurality of reflection values for a plurality of points along a light trace through the eye;
   calculating a plurality of combined values, wherein each combined value is obtained from several reflection values at different locations in said eye;
   using said reflection values for modelling at least one curved structure of the eye;
   calculating said combined values along a given axis by:
      using said reflection values for modelling at least a first and a second curved structure in the eye, wherein said first structure is located at a first position along said axis and said second structure is located at a second position along said axis; and for obtaining a combined value at a third position between said first and said second position, combining a third plurality of the reflection values of points from different A-scans, wherein said points are in a region between said first and said second structure.

17. The method of claim 16, wherein the points corresponding to the third plurality of the reflection values
are arranged tangentially along a curve interpolated from said first and said second structure or
comprise a first subset of points arranged tangentially along a first curve parallel to the first structure and a second subset of points arranged tangentially along a second curve parallel to the second, wherein said first and second curves intersect at said third position.

18. A method for obtaining data representing structures in an eye, in particular data representative of a cross-sectional image, by optical coherence tomography, said method comprising:
recording a set of A-scans, wherein at least some of said A-scans are recorded at different locations of the eye, and wherein each A-scan is used to generate a plurality of reflection values for a plurality of points along a light trace through the eye; and
calculating a plurality of combined values, wherein each combined value is obtained from several reflection values at different locations in said eye,
wherein the calculating of a plurality of combined values comprises not using reflection values of any A-scan exhibiting specular reflection but values of neighboring A-scans that do not exhibit specular reflection when calculating the combined values.

19. The method of claim 18, comprising using said reflection values for modelling at least one curved structure of the eye.

20. The method of claim 19, comprising using the modeled curved structure for identifying the points on a subset of the A-scans that are to be used for calculating the combined values.

21. The method of claim 20, comprising the step of calculating an estimate re (i) of an A-scan i in said subgroup for a given depth coordinate by interpolating at least two reflection values on said A-scan i closest to said depth coordinate.

* * * * *